(12) United States Patent
Spratt et al.

(10) Patent No.: US 8,613,746 B2
(45) Date of Patent: Dec. 24, 2013

(54) PREPARATORY REAMERS FOR ORTHOPEDIC IMPLANTS

(75) Inventors: Frank Spratt, Le Locle (CH); Henri Défossez, Le Locle (CH); Duncan Colin Betts, Le Locle (CH); Robert Hart, Portland, OR (US)

(73) Assignee: DePuy Synthes Products, LLC., Raynham, MA (US)

( * ) Notice: Subject to any disclaimer, the term of this patent is extended or adjusted under 35 U.S.C. 154(b) by 371 days.

(21) Appl. No.: 12/606,676

(22) Filed: Oct. 27, 2009

(65) Prior Publication Data

US 2011/0098710 A1  Apr. 28, 2011

(51) Int. Cl.
*A61B 17/00*  (2006.01)

(52) U.S. Cl.
USPC .......................................................... 606/80

(58) Field of Classification Search
USPC .............. 606/79–84; 408/223, 227, 228, 224
See application file for complete search history.

(56) References Cited

U.S. PATENT DOCUMENTS

| | | | | |
|---|---|---|---|---|
| 4,116,200 A * | 9/1978 | Braun et al. | ..................... | 606/81 |
| 5,549,613 A * | 8/1996 | Goble et al. | ..................... | 606/80 |
| 5,976,144 A * | 11/1999 | Fishbein et al. | ................ | 606/80 |
| 6,884,245 B2 * | 4/2005 | Spranza, III | .................... | 606/79 |
| 7,008,430 B2 | 3/2006 | Dong | | |
| 7,217,271 B2 | 5/2007 | Wolford | | |
| 7,553,313 B2 | 6/2009 | Bagby | | |
| 7,648,316 B2 * | 1/2010 | Ebert | ............................. | 408/227 |
| 2004/0193168 A1 | 9/2004 | Long | | |
| 2006/0217713 A1 | 9/2006 | Serhan | | |
| 2008/0255622 A1 | 10/2008 | Mickiewicz | | |

FOREIGN PATENT DOCUMENTS

WO   WO 2006105000   10/2006

OTHER PUBLICATIONS

DePuy AcroMed Product Catalog, Manual Instruments, Interbody Fusion, p. 2, Dec. 1999.

\* cited by examiner

*Primary Examiner* — Anu Ramana

(57) ABSTRACT

A reamer for preparing a spinal upper facet to facilitate insertion of combined screw/washer implant, preventing bone damage and facet weakening, and also allowing possibility to place grafting so as to maximize implant stabilization. The reamer has shallow outer cutting surfaces to cut a groove for spike insertion; deep inner cutting surfaces to cut a cortical-penetrating bore for insertion of the screw, and a flat therebetween to limit penetration of these cutting surfaces.

22 Claims, 8 Drawing Sheets

PREPARATORY REAMERS FOR ORTHOPEDIC IMPLANTS

BACKGROUND OF THE INVENTION

The vertebrae in a patient's spinal column are linked to one another by an intevertebral disc and facet joints. This three joint complex controls the movement of the vertebrae relative to one another. Each vertebra has a pair of articulating surfaces located on its left side, and a pair of articulating surfaces located on its right side, and each pair includes a superior articular surface and an inferior articular surface. Together the superior and inferior articular surfaces of adjacent vertebrae form a facet joint. Facet joints are synovial joints, which means that each joint is surrounded by a capsule of connective tissue and produces a fluid to nourish and lubricate the joint. The joint surfaces are coated with cartilage that allow the joints to move or articulate relative to one another.

Diseased, degenerated, impaired, or otherwise painful facet joints and/or discs can require surgery to stabilize the spine and relieve pain in the three joint complex. In the lumbar spine, for example, one form of treatment to stabilize the spine and relieve pain involves fusion of the facet joint.

One known technique for stabilizing and treating the facet joint involves a trans-facet fusion, in which pins, screws or bolts penetrate the lamina to fuse the joint. Such a technique has associated with it the risk of further injury to the patient, as such translamina facet instrumentation can be difficult to place in such a way that it does not violate the spinal canal and/or contact the dura of the spinal cord or the nerve root ganglia. Further, trans-facet instrumentation has been known to create rotational distortion, lateral offset, hyper-lordosis, and/or intervertebral foraminal stenosis at the level of instrumentation.

Examples of facet instrumentation currently used to stabilize the lumbar spine include trans-lamina facet screws ("TLFS") and trans-facet pedicle screws ("TFPS"). TLFS and TFPS implants provide reasonable mechanical stability, but, as noted above, they can be difficult to place, have long trajectories, and surgical access can be confounded by local anatomy. In some instances, these implants can result in some degree of foraminal stenosis.

US Patent Publication 2008-0255622 (DePuy Spine), the specification of which is incorporated by reference in its entirety, discloses spinal implants and methods relating to stabilization and/or fusion of a facet joint via trans-facet and intra-facet delivery of the implants. In general, the implant functions as a sort of mechanical staple and/or key that prevents sliding motion between the diarthroidal surfaces of the facet joint. Further, the spinal implant can include a fusion-promoting bioactive material thereby providing for a single spinal implant capable of allowing for both fixation and fusion of a desired facet joint. In particular, it discloses facet fixation and fusion washer and screw assemblies.

It is an object of the present invention to prepare the spinal upper facet to facilitate insertion of such combined screw/washer implants, thereby preventing bone damage and facet weakening, and also allowing the placing of graft therein so as to maximize implant stabilization.

The art discloses a number of bone reamers.

U.S. Pat. No. 7,008,430 (Dong) discloses a positioning tool for a joint socket cutting instrument or an implant for use with a minimally invasive surgical procedure and in conjunction with a computer assisted surgical procedure. The positioning tool has a longitudinally extending drive shaft having a moveable joint at a first end and a drive coupling for connecting to a power source at a second end. A holder for mounting a cutting tool such as a drill or as an acetabular cutting instrument or for mounting an acetabular implant is coupled to the moveable joint at the first end of the drive shaft for movement with respect to the drive shaft. The holder is rotatable about a central axis thereof when the drive shaft is rotated. The drive shaft includes a shaft bearing mounted thereon which is pivotally coupled to the shaft at a fixed longitudinal position and is pivotally coupled to a longitudinally extending first arm having a handle. A tracker system which is capable of being utilized by a computer-aided surgical system is mounted on the first arm. A second arm is provided which is pivotally connected to the holder at a first end and pivotally connected to the first arm at a second end. The resulting four bar linkage allows the holder and the cutting instrument/implant to be manipulated in any position while the known geometric relationship between the tracker and the holder allows the location of the holder to be displayed by the computer on a cathode ray tube with respect to a joint.

PCT Patent Publication WO 2006/105000 (Chervitz) discloses a reamer designed to engage a guide member, such as a guide wire, implanted in bone at any of a plurality of relative orientations such that the resulting resection of the bone does not depend on the relative orientation. The reamer may have a shaft that receives torque and a reaming head with a cavity into which a protruding portion of the guide wire is insertable. The cavity may have a generally conical shape capable of receiving the guide wire at a variety of relative orientations. The orientation of the reaming head is determined not by that of the guide wire, but by a stationary frame to which the reamer is coupled. The reamer may optionally have an offset assembly that causes the reaming head to rotate about an axis displaced from that of the shaft to reduce the size of the incision required to reaming head.

U.S. Pat. No. 7,553,313 (Bagby) discloses an apparatus for preparing a spinal implant surgical site for receiving a spinal fusion implant. The apparatus includes a drive shaft, a handle, and a hollow, cylindrical cutting body. The handle is carried by the drive shaft, the hollow, cylindrical cutting body is provided at a leading end of the drive shaft. The cylindrical cutting body has an open leading end, a plurality of circumferentially spaced-apart cutting teeth provided on the open leading end, and a plurality of circumferentially spaced-apart gullets each provided between an adjacent pair of the cutting teeth.

SUMMARY OF THE INVENTION

It is an object of the present invention to prepare a spinal upper facet to facilitate insertion of a combined screw/washer implant, preventing bone damage and facet weakening, and also allowing possibility to place grafting so as to maximize implant stabilization.

In accordance with the present invention, there is provided a bone reamer having a cutting bit comprising:
 a) a plurality of shallow outer cutting surfaces to cut a groove for spike insertion;
 b) a plurality of deep inner cutting surfaces to cut a cortical-penetrating bore for insertion of the screw, and
 c) a flat therebetween to limit penetration of these cutting surfaces.

Each of these regions of the cutting bit will now be discussed in more detail.

A first region is made up of the circumferentially-disposed outer cutting surfaces. When the bit is rotated, these surfaces cut a thin groove within the upper facet, thereby allowing for easy penetration of the spikes of the washer. The depth (or height) of these cutting surfaces is shallow, in order to allow initial reaming of the cortical bone while still preventing significant weakening the facet. Preferably, the depth of these outer cutting surfaces is less than 3 mm, and is more preferably about 1.25 mm. The widths of the outer cutting surfaces are slightly undersized in comparison to the thickness of the spikes of the washer. In this condition, the spike creates an interference fit in the groove.

A second region is made up of the inner cutting surfaces. These surfaces counter-bore the bone to allow space for the screw head, thereby reducing the possibility of the bone splitting during screw insertion. Additionally, the counter-bore allows the insertion of graft material under the screw head and washer implant components.

A third region of the bit is represented by a flat region between the inner and outer cutting surfaces. This flat limits the cutting depth of the instrument, and so prevents weakening of the facet.

Therefore, in accordance with the present invention, there is provided a drill bit for preparatory reaming of a spinal facet surface, comprising:
- a) a shaft having a proximal end portion and a distal end portion,
- b) a drill attachment feature extending from the proximal end portion of the shaft, and
- c) a cutting bit extending from the distal end portion of the shaft, wherein the cutting bit has a distal face comprising:
- i) a plurality of circumferentially-disposed inner cutting surfaces having a height,
- ii) a plurality of circumferentially-disposed outer cutting surfaces having a height, and
- iii) a circumferential flat located radially outside the inner cutting surfaces, wherein height of the inner cutting surfaces is greater than the height of the outer cutting surfaces.

DESCRIPTION OF THE FIGURES

FIG. 1b discloses a perspective view of a cutting bit of the drill bit of FIG. 1a.

DETAILED DESCRIPTION OF THE INVENTION

Figure 1A:
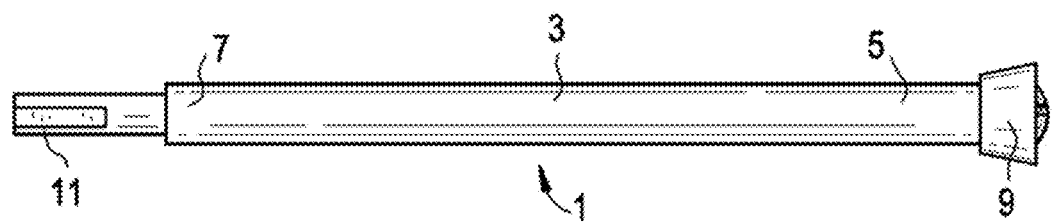
FIG. 1a discloses a side view of a drill bit of the present invention.
Figure 1B:
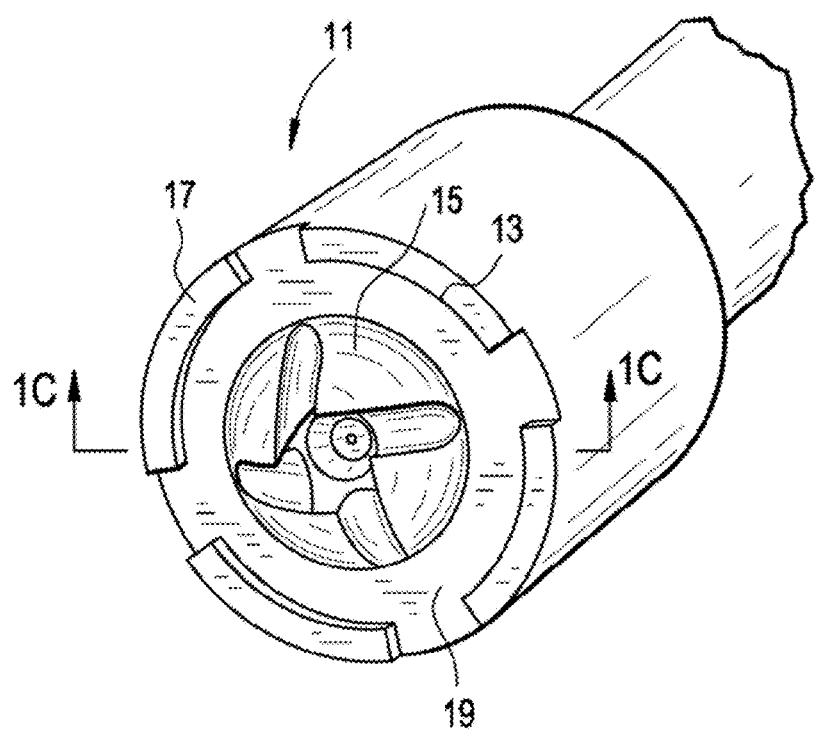

Now referring to FIGS. 1a and 1b, there is provided a drill bit 1 for preparatory reaming of a spinal facet surface, comprising:
- a) a shaft 3 having a proximal end portion 5 and a distal end portion 7,
- b) a drill attachment feature 9 extending from the proximal end portion of the shaft, and
- c) a cutting bit 11 extending from the distal end portion of the shaft, wherein the cutting bit has a distal face 13 comprising:
- i) a plurality of circumferentially-disposed inner cutting surfaces 15,
- ii) a plurality of circumferentially-disposed outer cutting surfaces 17, and
- iii) a circumferential flat 19 located radially outside the inner cutting surfaces.

Figure 1C:
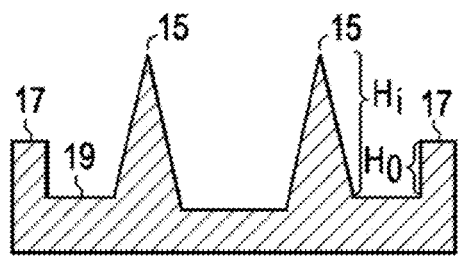
FIG. 1c discloses a cross-section of the cutting bit of FIG. 1b.

Now referring to FIG. 1c, the inner cutting surfaces 15 have a height $H_i$ and the outer cutting surfaces 17 have a height $H_o$, and the height $H_i$ of the inner cutting surfaces is greater than the height $H_o$ of the outer cutting surfaces. In this embodiment, the greater height of the inner cutting surface allows the surgeon to fully penetrate the cortical bone in the region meant for insertion of the screw portion of the implant without penetrating the cortical bone region meant for the spike portion of the implant. Preferably, the height of the inner cutting surfaces is at least 2 times greater than the height $H_o$ of the outer cutting surfaces. More preferably, the height of the inner cutting surfaces is at least 5 times greater than the height $H_o$ of the outer cutting surfaces.

In some embodiments, as in FIG. 1b, at least a portion of the circumferential flat is located between the inner cutting surfaces and the outer cutting surfaces. Typically, another portion of the circumferential flat is located radially outside the outer cutting surfaces. In other embodiments (not shown), however, the circumferential flat may be radially located solely outside the outer cutting surfaces.

Figure 2:
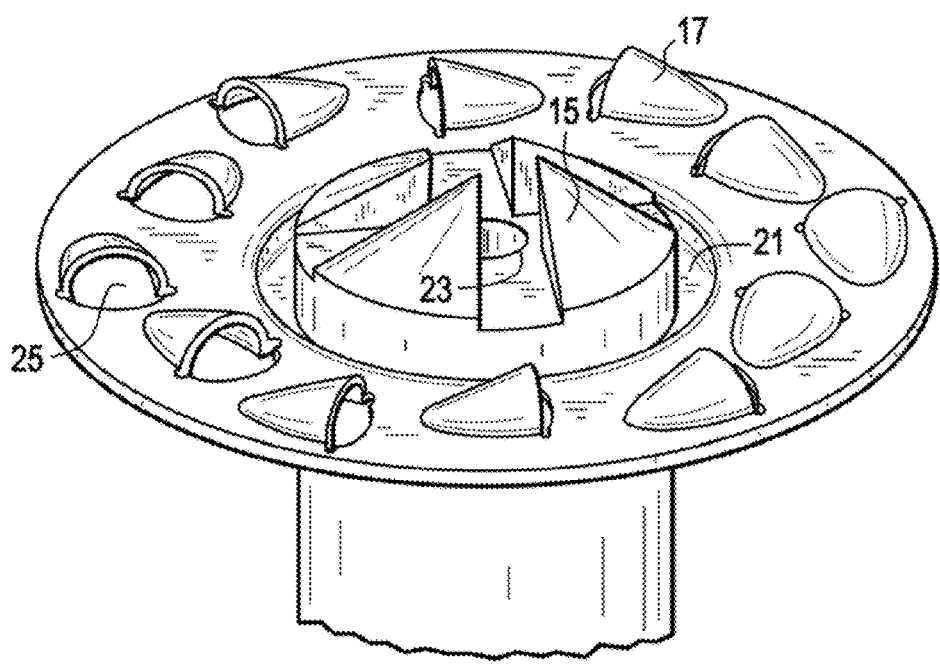
FIG. 2 discloses a perspective view of a cutting bit of the present invention having a grater feature.

In some embodiments, and now referring to FIG. 2, the distal face of the cutting bit further comprises iv) a circumferential depression 21 located between the inner cutting surfaces 15 and the outer cutting surfaces 17. This depression provides a place for bone debris, thereby cleaning the targeted region of debris and allowing for more precise reaming.

Still referring to FIG. 2, in some embodiments, the circumferential flat is located both radially inside and outside the outer cutting surfaces, thereby providing even greater stability and precision in limiting the cutting depth of the instrument, and so prevents weakening of the facet to an even greater extent.

Still referring to FIG. 2, in some embodiments, the cutting bit further comprises iv) a bore 23 located radially inside the inner cutting surfaces. This bore may receive a guide wire to allow highly controlled reaming.

Still referring to FIG. 2, in some embodiments, each outer cutting surface forms an opening 25 in the distal face of the cutting bit. These openings act as flutes that channel debris away from the bone-cutting bit interface, thereby allowing a more clean and precise cut.

Figure 3:
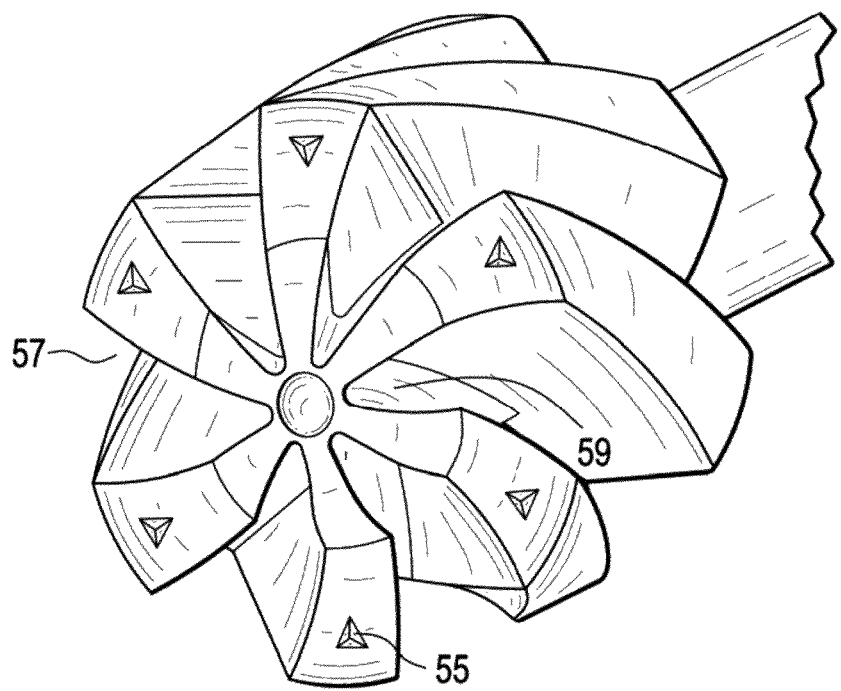
FIG. 3 discloses a perspective view of a cutting bit of the present invention having flutes.

Now referring to FIG. 3, in some embodiments, each of the outer cutting surfaces has a pyramidal shape 55. The pyramidal shape is a preferred cutting shape, as it allows a gradually larger cut to be made.

Still referring to FIG. 3, in some embodiments, the drill bit further comprises d) a first plurality of cutting flutes 57 located between the outer cutting surfaces.

Still referring to FIG. 3, in some embodiments, the drill bit further comprises e) a second plurality of cutting flutes 59 located between the inner cutting surfaces. These flutes channel debris away from the bone-cutting bit interface, thereby allowing a more clean and precise cut.

Figure 4:
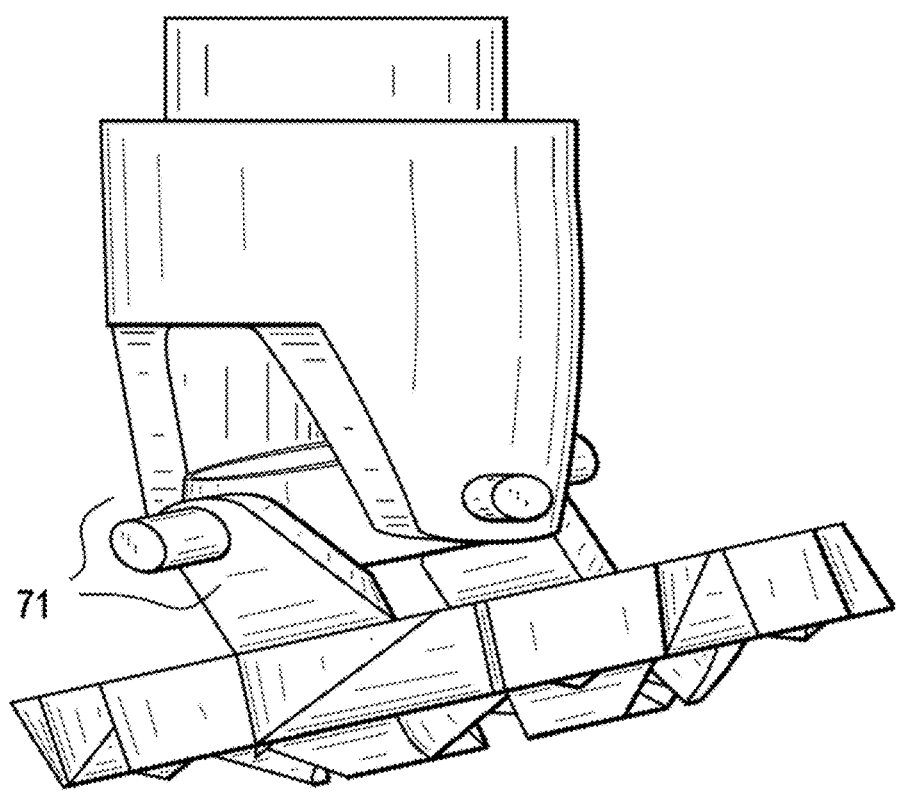
FIG. 4 discloses a perspective view of a cutting bit of the present invention connected to a shaft by a universal joint.

Now referring to FIG. 4, in some embodiments, the cutting bit is adapted to pivot about the distal end portion of the shaft. In some embodiments thereof, the distal end portion of the shaft and the cutting bit comprises a pivoting means 71. In some embodiments, the pivoting means comprises a universal joint (as shown).

Figure 5:
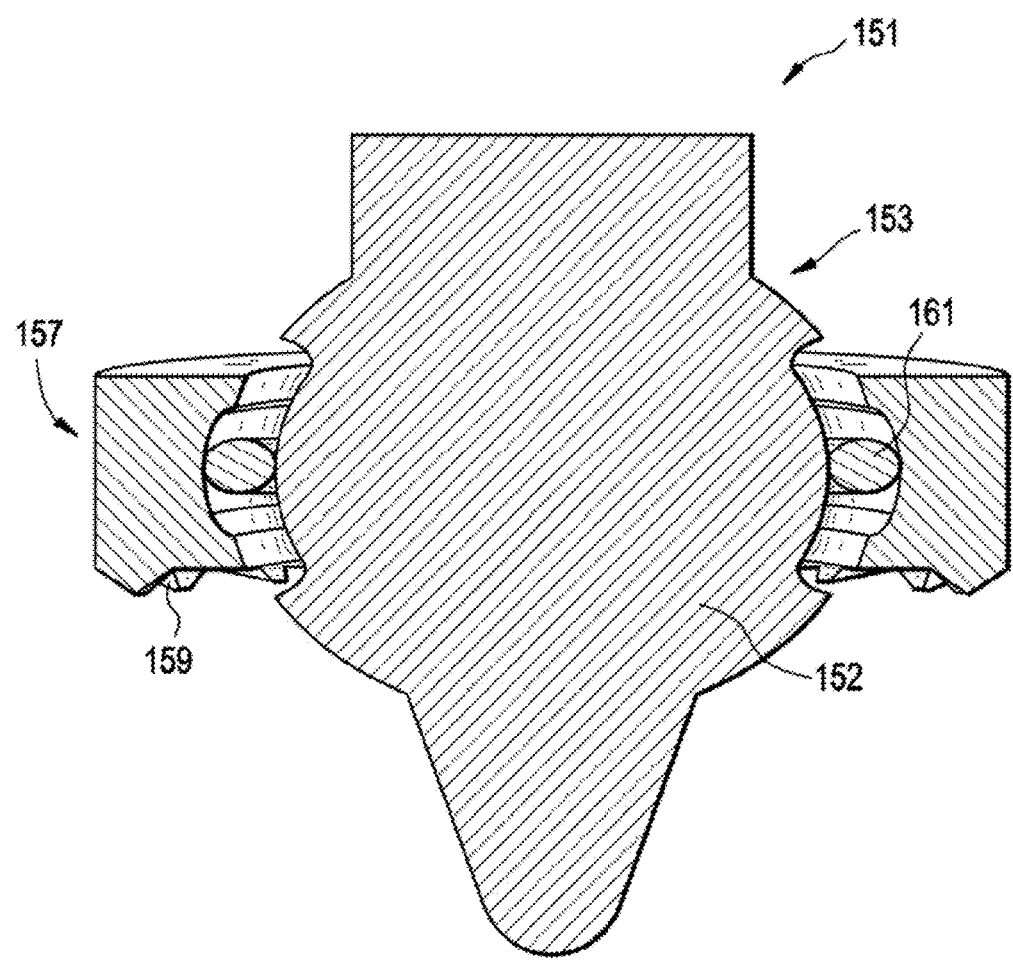
FIG. 5 discloses a side view of a cutting bit of the present invention connected to a shaft by a polyaxial joint.

Now referring to FIG. 5, in some embodiments, the pivoting means comprises a polyaxial joint. Additionally, the polyaxial options incorporate angulation of the cutting face around the cutting tip. This also allows reaming over a guide wire. In this case, the device includes a universal joint or rzeppa joint and uses ball bearings to drive the cutting face.

Now therefore, in accordance with the present invention, there is provided a drill bit for preparatory reaming of a spinal facet surface, comprising:
 a) a shaft having a proximal end portion and a distal end portion,
 b) a drill attachment feature extending from the proximal end portion of the shaft, and
 c) a cutting bit extending from the distal end portion of the shaft,
wherein the cutting bit 151 has a distal face 152 comprising:
  i) an inner region 153 comprising a plurality of circumferentially-disposed inner cutting surfaces,
  ii) an outer region 157 comprising a plurality of circumferentially-disposed outer cutting surfaces 159, and
  iii) a plurality of force transfer elements 161 (such as a bearing ball) contacting the inner and outer regions.

Preferably, the shaft of this device is cannulated. Also preferably, the height of the inner cutting surfaces is greater than the height of the outer cutting surfaces.

Generally, the drill bit of the present invention is made of a high hardness biocompatible material such as a metal or ceramic. Preferably, the metal is stainless steel.

Also in accordance with the present invention, there is provided a method of preparing a spinal facet surface, comprising the steps of:
 a) contacting the drill bit of the present invention against the spinal facet surface, and
 b) rotating the drill bit upon the spinal facet surface so as to produce a prepared spinal facet surface having an inner circular recess and a coaxial outer circular recess.

In preferred embodiments, the method further comprises the step of c) inserting an implant (such as a facet screw) into the inner and outer circular recesses of the prepared spinal facet surface. Generally, the implant has a washer having a plurality of circumferentially-disposed spikes extending therefrom. These spikes correspond to the outer circular recess of the prepared spinal facet surface. More specifically, the implant spikes have a width, the outer circular recess has a width, and the width of the spikes is slightly greater than the width of the outer circular recess. In this condition, the spikes are interference fitted into the recess.

Also preferably, the drill bit may further comprise a throughbore located radially inside the inner cutting surfaces. In such embodiments, the method may further comprise the step of inserting a guide wire into the throughbore. The use of a guide wire may provide for highly controlled cutting.

In some embodiments, the drill bit has a drill attachment feature 9 extending from the proximal end portion of the shaft. This feature allows the bit's connection to a high speed drill.

Therefore, in accordance with the present invention, there is provided an assembly comprising:
 a) a high-speed drill having a drill bit attachment collet, and
 b) the drill bit of the present invention having a drill bit attachment feature,
wherein the drill attachment feature is secured in the collet of the drill.

In preferred embodiments of this assembly, drill bit further comprises a bore located radially inside the inner cutting surfaces. A guide wire may then be located in the bore in order to provide highly controlled cutting.

Figure 6:
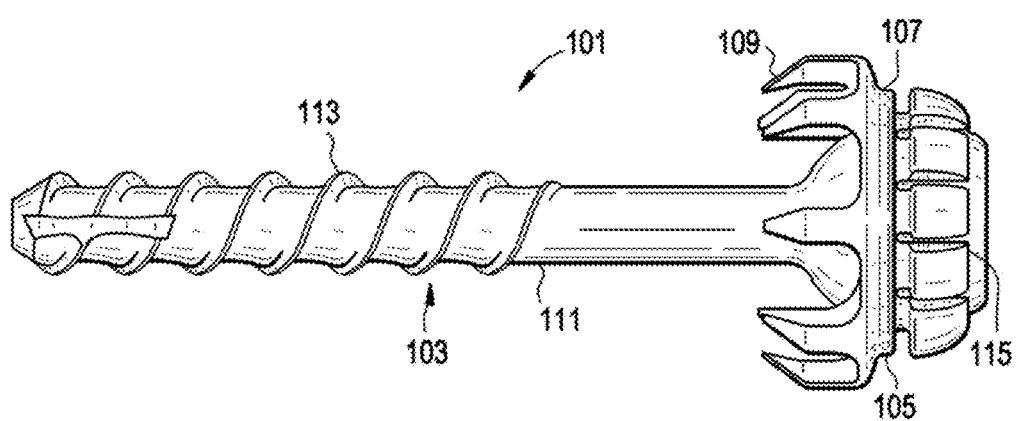
FIG. 6 discloses a facet screw that may be used in accordance with the method of the present invention.

Now referring to FIG. 6, there is provided an exemplary implant 101 to be used in accordance with the present invention. The implant comprises a facet screw 103 and a washer 105. The washer has a base plate 107 and a plurality of spikes 109 dedicated to penetrating the bone, so as to maximize stability. The washer also has a central bore (not shown) through which the screw extends. The facet screw has a shaft 111 having a threaded region 113 formed thereon, and a large round proximal head 115 which allows washer polyaxiality. These components are preferably made of a biocompatible material; preferably stainless steel or titanium.

Figure 7:
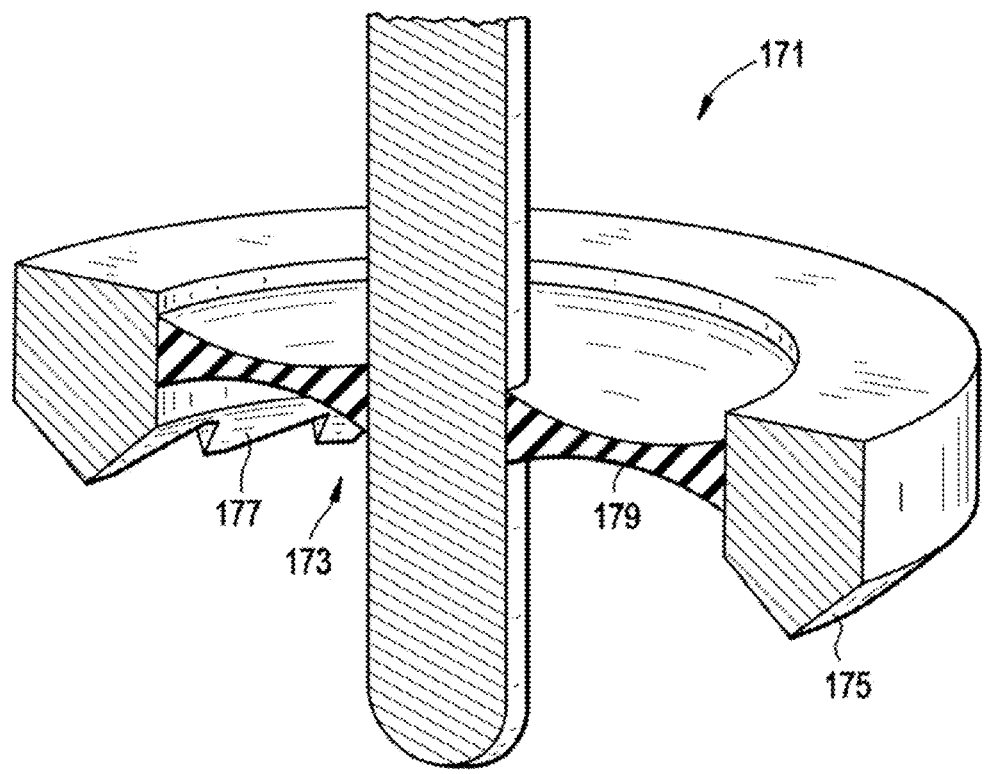
FIG. 7 discloses an additional embodiment of the present invention in which a flexible membrane connects the inner and outer cutting regions.

Now referring to FIG. 7, there is provided an additional embodiment of the present invention. This embodiment uses a flexible membrane to connect the inner and outer cutting regions. The cutting faces can articulate by deforming a flexible membrane. This deformation allows for pressure compensation. In preferred embodiments, the membrane is made of a biocompatible polymer, such as an elastomer, which allows for equal pressure to be applied throughout the cutting surface.

Now therefore, in accordance with the present invention, there is provided a drill bit for preparatory reaming of a spinal facet surface, comprising:
 a) a shaft having a proximal end portion and a distal end portion,
 b) a drill attachment feature extending from the proximal end portion of the shaft, and
 c) a cutting bit extending from the distal end portion of the shaft,
wherein the cutting bit 171 has a distal face comprising:
  i) an inner region 173 comprising a plurality of circumferentially-disposed inner cutting surfaces,
  ii) an outer region 175 comprising a plurality of circumferentially-disposed outer cutting surfaces 177, and
  iii) a flexible membrane 179 connected the inner and outer regions.

Preferably, the shaft of this device is cannulated. Also preferably, the height of the inner cutting surfaces is greater than the height of the outer cutting surfaces.

Figure 8A:
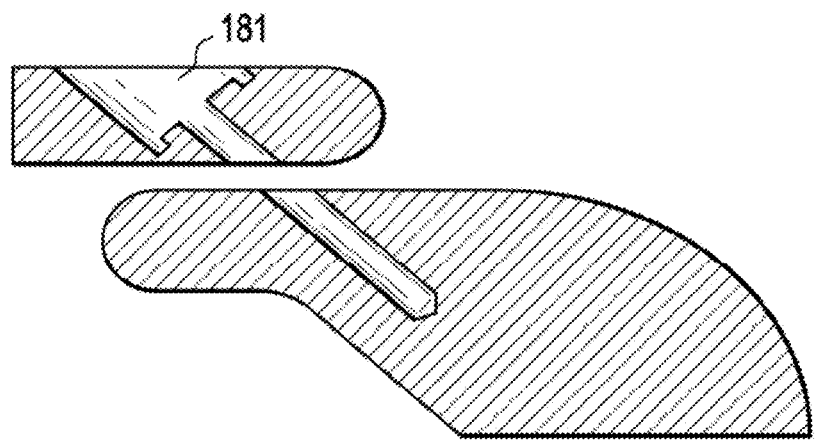
FIGS. 8a and 8b provide a cross section of the profiles made in a facet joint by conventional and polyaxial reamers.
Figure 8B:
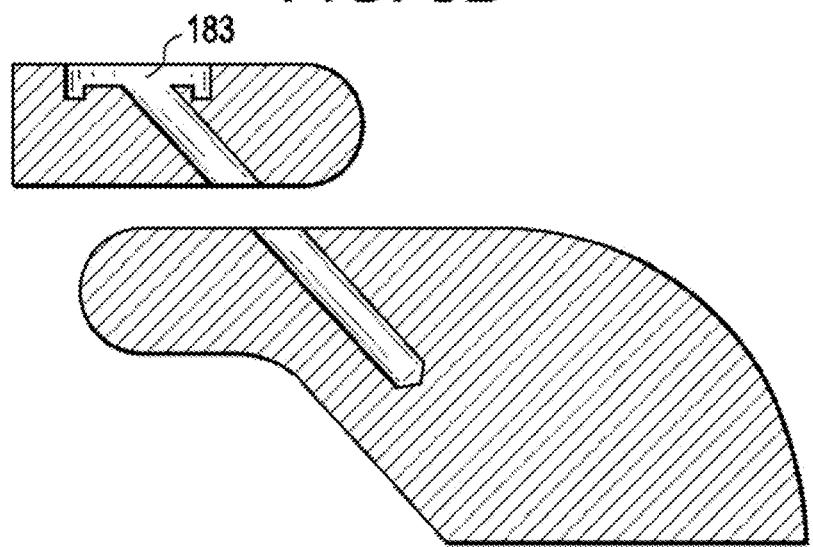

Now referring to FIGS. 8a and 8b, there is provided a comparison of material removed by a standard reamer 181 versus a polyaxial reamer of the present invention 183, when reaming over a guidewire or down a port. Because the polyaxial reamer adapts to the bone surface, it removes far less material for the equivalent profile. Therefore, it accomplishes the reaming function with substantially less degradation of the bone strength.

We claim:

1. A drill bit for preparatory reaming of a spinal facet surface, comprising:
 a) a shaft having a proximal end portion and a distal end portion,
 b) a drill attachment feature extending from the proximal end portion of the shaft, and
 c) a cutting bit extending from the distal end portion of the shaft,
wherein the cutting bit has a distal face comprising:
  i) a plurality of circumferentially-disposed inner cutting surfaces having a height,
  ii) a plurality of circumferentially-disposed outer cutting surfaces having a height, and
  iii) a planar circumferential flat located radially between the inner cutting surfaces and the outer cutting surfaces, wherein the heights are measured with respect to the circumferential flat, wherein the height of an inner cutting surface is greater than the height of an outer cutting surface.

2. The drill bit of claim 1 wherein the circumferential flat is located radially outside the outer cutting surfaces.

3. The drill bit of claim 2 wherein the distal face of the cutting bit further comprises:
 iv) a circumferential depression located between the inner cutting surfaces and the outer cutting surfaces.

4. The drill bit of claim 1 wherein the circumferential flat is located both radially inside and outside the outer cutting surfaces.

5. The drill bit of claim 1 further comprising:
 d) a bore located radially inside the inner cutting surfaces.

6. The drill bit of claim 1 wherein each of the outer cutting surfaces has a pyramidal shape.

7. The drill bit of claim 1 wherein each outer cutting surface forms an opening in the distal face of the cutting bit.

8. The drill bit of claim 7 further comprising:
 d) a second plurality of cutting flutes located between the inner cutting surfaces.

9. The drill bit of claim 1 further comprising:
 d) a first plurality of cutting flutes located between the outer cutting surfaces.

10. The drill bit of claim 1 wherein the cutting bit is adapted to pivot about the distal end portion of the shaft.

11. The drill bit of claim 1 wherein the height of the inner cutting surfaces is at least 2 times greater than the height of the outer cutting surfaces.

12. The drill bit of claim 11 wherein the height of the inner cutting surfaces is at least 5 times greater than the height of the outer cutting surfaces.

13. The drill bit of claim 1 wherein the shaft is cannulated.

14. A method of preparing a spinal facet surface, comprising the steps of:
 a) contacting the drill bit of claim 1 against the spinal facet surface, and
 b) rotating the drill bit upon the spinal facet surface so as to produce a prepared spinal facet surface having an inner circular recess and an outer circular recess.

15. The method of claim 14, further comprising the step of:
 c) inserting an implant into the inner and outer circular recesses of the prepared spinal facet surface.

16. The method of claim 15, wherein the implant has a plurality of circumferentially-disposed spikes corresponding to the outer circular recess of the prepared spinal facet surface.

17. The method of claim 15, wherein the implant spikes have a width, and the outer circular recess has a width, and wherein the width of the spikes is slightly greater than the width of the outer circular recess to provide an interference fit therein.

18. The method of claim 15, wherein the drill bit further comprises a throughbore bore located radially inside the inner cutting surfaces, wherein the method further comprises the step of:
 d) inserting a guide wire into the throughbore.

19. An assembly comprising:
 a) a high-speed drill having a drill bit attachment collet,
 b) the drill bit of claim 1 having a drill bit attachment feature,
wherein the drill attachment feature is secured in the collet of the drill.

20. The assembly of claim 19 wherein the drill bit further comprises:
 iv) a bore located radially inside the inner cutting surfaces.

21. The assembly of claim 20 further comprising:
 c) a guide wire located in the bore.

22. A drill bit for preparatory reaming of a spinal facet surface, comprising:
 a) a shaft having a proximal end portion and a distal end portion,
 b) a drill attachment feature extending from the proximal end portion of the shaft, and
 c) a cutting bit extending from the distal end portion of the shaft,
wherein the cutting bit has a planar distal face comprising:
 i) an inner region comprising a plurality of circumferentially-disposed inner cutting surfaces,
 ii) an outer region comprising a plurality of circumferentially-disposed outer cutting surfaces, and
 iii) a flexible membrane connected the inner and outer regions,
wherein the flexible membrane is configured to deform, allowing for equal pressure to be applied throughout the inner and outer cutting surfaces.

\* \* \* \* \*